United States Patent [19]
Rodriguez

[11] Patent Number: 5,709,236
[45] Date of Patent: Jan. 20, 1998

[54] COLOSTOMY POUCH RINSING DEVICE

[76] Inventor: Ernest L. Rodriguez, 15736 Wedgeworth Dr., Hacienda Heights, Calif. 91745

[21] Appl. No.: 743,009

[22] Filed: Nov. 1, 1996

[51] Int. Cl.⁶ .................................................. B08B 3/02
[52] U.S. Cl. ........................... 134/167 R; 134/169 R; 134/172; 134/201; 134/198; 604/277; 604/334
[58] Field of Search ........................... 134/166 R, 167 R, 134/168 R, 169 R, 201, 172, 198; 604/277, 355, 334; 239/525, 530

[56] References Cited

U.S. PATENT DOCUMENTS

| | | | |
|---|---|---|---|
| 466,680 | 1/1892 | Harris et al. | 134/167 R |
| 1,528,081 | 3/1925 | Schermerhorn et al. | 134/166 C |
| 1,687,012 | 10/1928 | Forth | 134/166 R |
| 1,745,323 | 1/1930 | Coe et al. | 239/530 |
| 1,985,813 | 12/1934 | Baden | 134/166 C |
| 3,003,506 | 10/1961 | Wolsicki | 134/167 R |
| 3,605,135 | 9/1971 | Tan | 134/166 C |
| 4,194,506 | 3/1980 | Voorhees | 604/334 |
| 5,095,503 | 3/1992 | Wellman | 134/167 R |
| 5,133,374 | 7/1992 | Druding et al. | 134/169 R |
| 5,387,182 | 2/1995 | Otani . | |
| 5,454,389 | 10/1995 | Hubbard et al. | 134/166 R |
| 5,485,857 | 1/1996 | Amundsen | 134/166 C |

*Primary Examiner*—Frankie L. Stinson

[57] ABSTRACT

A colostomy pouch rinsing device comprises a faucet coupling assembly including a central elbow member having an upper section including faucet coupling devices and a lower section including a first compression unit; a water control handle including a main body and a control lever coupled thereto; a rubber hose having an inboard end being coupled to the faucet coupling assembly, the outboard end of the hose being coupled to the water control handle; a spray head formed in a hollow, generally cylindrical configuration with an upper end including a plurality of water apertures projecting therethrough; and copper tubing with an inboard end being threadedly coupled to the projection member of the handle and an outboard end formed contiguously with the spray head.

7 Claims, 3 Drawing Sheets

COLOSTOMY POUCH RINSING DEVICE

BACKGROUND OF THE INVENTION

1. Field of the Invention

The present invention relates to an colostomy pouch rinsing device and more particularly pertains to hygienically cleansing colostomy pouches.

2. Description of the Prior Art

The use of body waste container cleaning devices is known in the prior art. More specifically, body waste container cleaning devices heretofore devised and utilized for the purpose of cleaning various types of body waste containers are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,194,506 to Voorhies discloses a kit for an ostomate.

U.S. Pat. No. 5,096,503 to Wellman discloses a body waste bag washer.

U.S. Pat. No. Des. 257,537 to Chow et al. discloses a spray wand.

U.S. Pat. No. 4,941,878 to Petrik discloses an ostomy pouch flusher.

U.S. Pat. No. 5,387,182 to Otani discloses a faucet mounted water jet dental hygiene apparatus.

U.S. Pat. No. 4,134,404 to Williams, Jr. discloses a portable colostomy kit.

While these devices fulfill their respective, particular objective and requirements, the aforementioned patents do not describe an colostomy pouch rinsing device for hygienically cleansing colostomy pouches.

In this respect, the colostomy pouch rinsing device according to the present invention substantially departs from the conventional concepts and designs of the prior art, and in doing so provides an apparatus primarily developed for the purpose of hygienically cleansing colostomy pouches.

Therefore, it can be appreciated that there exists a continuing need for new and improved colostomy pouch rinsing device which can be used for hygienically cleansing colostomy pouches. In this regard, the present invention substantially fulfills this need.

SUMMARY OF THE INVENTION

In the view of the foregoing disadvantages inherent in the known types of body waste container cleaning devices now present in the prior art, the present invention provides an improved colostomy pouch rinsing device. As such, the general purpose of the present invention, which will be described subsequently in greater detail, is to provide a new and improved colostomy pouch rinsing device and method which has all the advantages of the prior art and none of the disadvantages.

To attain this, the present invention essentially comprises a new and improved colostomy pouch rinsing device for use in association with a faucet including a head and water, the apparatus comprising, in combination: a colostomy pouch formed in a generally rectangular configuration with a front, a top and a bottom, the front including attachment means to couple the pouch to a patient's abdomen, the bottom including a generally cylindrical aperture therein; a faucet coupling assembly including a central elbow member formed in a hollow generally cylindrical configuration and contoured in an L-shaped orientation, the faucet coupling assembly having an upper section including faucet coupling means and a lower section including a first compression unit, the upper and lower sections each being threadedly coupled to the central elbow member, the faucet coupling means comprising a inner section including male screw threads and an outer section including a snap-on coupling, the male screw threads being coupled within a faucet head, the outer section being securely fastened around a faucet head, the outer section including cross-hatching to frictionally engage the upper section, the first compression unit regulating the flow of water therethrough, the upper and lower sections having smaller diameter than the central elbow member; a water control handle including a main body and a L-shaped control lever hingedly coupled thereto, the main body being formed in a generally cylindrical configuration and having a central region, an inboard end, an outboard end and a hollow interior, the outboard end including a projection member extending therefrom, the projection member having a hollow interior and including male screw threads therearound, the central region including a pin projecting therefrom, in an operative orientation a user grasping the control lever thereby depressing the pin and actuating the flow of water, the inboard end including a handle sleeve being formed in a hollow, generally conical configuration with first and second open free ends, the first free end being coupled to the handle, a reducer, PVC tubing and a second compression unit being positioned within the handle sleeve and regulating the flow of water therethrough, the compression unit and reducer each being threadedly coupled to the PVC tubing; a flexible rubber hose having an inboard end, an outboard end and a length of six feet, the inboard end of the hose being coupled to the first compression unit of the faucet coupling assembly, the outboard end of the hose being positioned through the second free end of the handle sleeve and coupled to the second compression unit; a spray head formed in a hollow, generally cylindrical configuration with a upper end and a lower end, the upper end having a greater diameter than the lower end, the upper end including a plurality of water apertures projecting therethrough; and copper tubing formed in a elongated generally cylindrical configuration and contoured as a loop with an inboard end and outboard end, the inboard end being positioned horizontally and including a nut, a rubber seal and a PVC washer, the inboard end of the copper tubing being threadedly coupled to the projection member of the handle and secured by the nut, the outboard end of the copper tubing being positioned vertically and being formed contiguously with the lower end of the spray head, in an operative orientation a user placing the spray head within the cylindrical aperture in the colostomy pouch, the user then connecting the faucet coupling assembly to a faucet and turning on the water, the user regulating the flow of water with the water control handle and washing the colostomy pouch.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved colostomy pouch rinsing device which has all the advantages of the prior art body waste container cleaning devices and none of the disadvantages.

It is another object of the present invention to provide a new and improved colostomy pouch rinsing device which may be easily and efficiently manufactured and marketed.

It is a further object of the present invention to provide a new and improved colostomy pouch rinsing device which is of durable and reliable construction.

An even further object of the present invention is to provide a new and improved colostomy pouch rinsing device which is susceptible of a low cost of manufacture with regard to both materials and labor, and which accordingly is then susceptible of low prices of sale to the consuming public, thereby making such an colostomy pouch rinsing device economically available to the buying public.

Still yet another object of the present invention is to provide a new and improved colostomy pouch rinsing device which provides in the apparatuses and methods of the prior art some of the advantages thereof, while simultaneously overcoming some of the disadvantages normally associated therewith.

Even still another object of the present invention is to provide a new and improved colostomy pouch rinsing device for hygienically cleansing colostomy pouches.

Lastly, it is an object of the present invention to provide a new and improved colostomy pouch rinsing device comprising: a faucet coupling assembly including a central elbow member formed in a hollow generally cylindrical configuration, an upper section and a lower section, the upper section including faucet coupling means and a lower section including a first compression unit, the upper and lower sections each being coupled to the central elbow member; a water control handle including a main body and a control lever coupled thereto, the main body having a central region, an inboard end including a handle sleeve, an outboard end and a hollow interior, the outboard end including a projection member extending therefrom, the central region including a pin projecting therefrom; a rubber hose having an inboard end being coupled to the faucet coupling assembly, the outboard end of the hose being coupled to handle sleeve; a spray head formed in a hollow, generally cylindrical configuration with an upper end including a plurality of water apertures projecting therethrough; and copper tubing with an inboard end being threadedly coupled to the projection member of the handle and an outboard end formed contiguously with the spray head, in an operative orientation a user placing the spray head within a colostomy pouch and connecting the faucet coupling assembly to a faucet, the user regulating the flow of water with the water control handle and washing the colostomy pouch.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
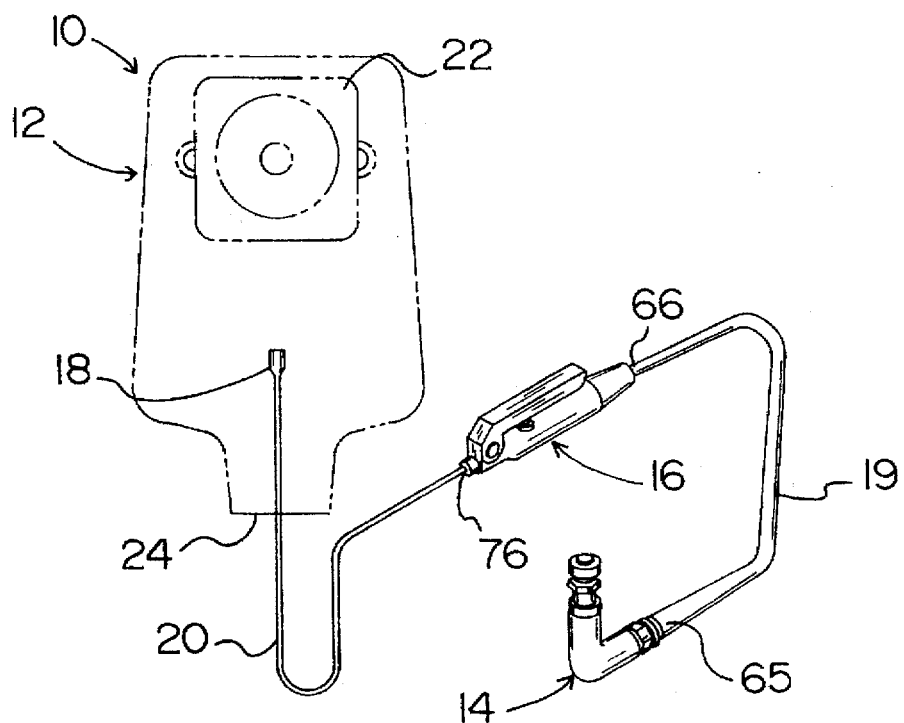
FIG. 1 is a perspective view of the preferred embodiment of the colostomy pouch rinsing device constructed in accordance with the principles of the present invention.

With reference now to the drawings, and in particular, to FIG. 1 thereof, the preferred embodiment of the new and improved colostomy pouch rinsing device embodying the principles and concepts of the present invention and generally designated by the reference number 10 will be described.

Specifically, it will be noted in the various Figures that the device relates to a new and improved colostomy pouch rinsing device 10. In its broadest context, the device consists of a colostomy pouch 12, a faucet coupling assembly 14, a water control handle 16, a spray head 18, copper tubing 20. Such components are individually configured and correlated with respect to each other so as to attain the desired objective.

The colostomy pouch rinsing device 10 is designed for use in association with a conventional faucet. Conventional faucets include a round faucet head with female threaded coupling means. Running water is used to clean the pouch. A user would hold the pouch over a toilet and flush out the bag with water. This enables a user to reuse the pouches several times and therefore minimizes expenses. This is a clean, safe, sanitary method of removing waste from within the bag. Note FIG. 1.

The colostomy pouch 12 formed in a generally rectangular configuration with a front, a top, a bottom and a hollow interior. In the preferred embodiment of the apparatus the pouch is fabricated of durable high-grade rubber or plastic. The colostomy pouch 12 is adapted to retain human waste of a patient with a bowel resection or other major bowel surgery. The front of the pouch includes attachment means 22 to couple the pouch to a patient's abdomen. The bottom of the pouch includes a generally cylindrical aperture 24. The aperture is used to empty the pouch. In alternative embodiments of the apparatus, a colostomy pouch is not included. Rather, in such embodiments the apparatus is used with an existing pouch. Note FIG. 1.

Figure 4:
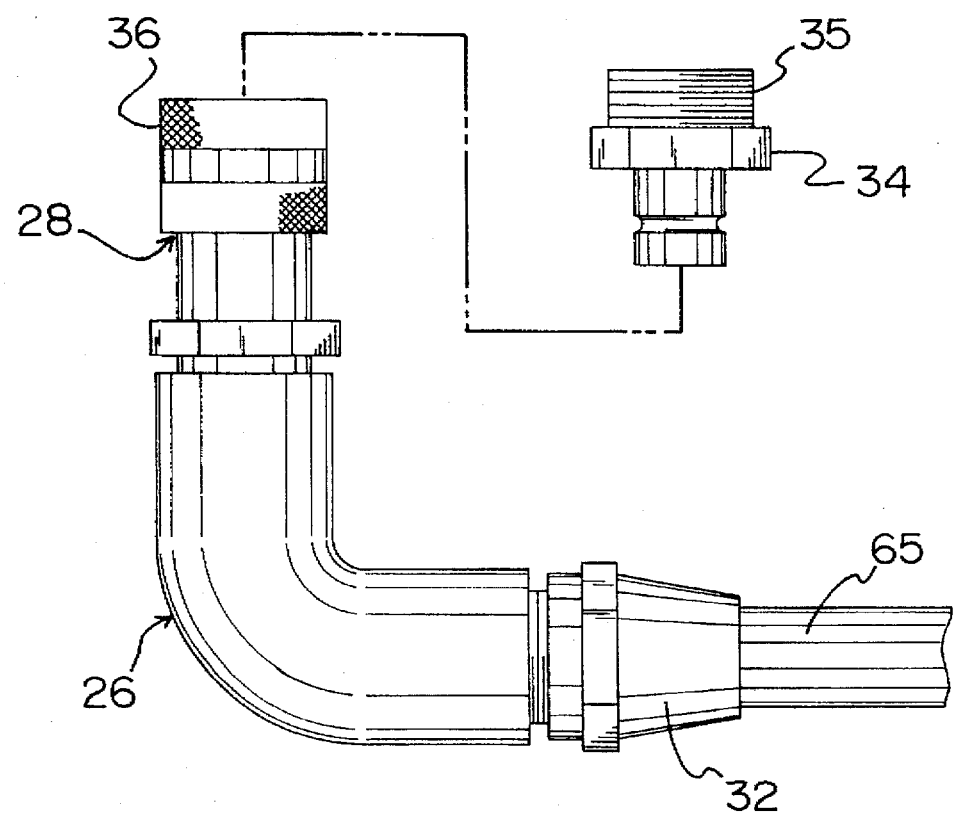
FIG. 4 is a separated perspective view of the faucet coupling assembly of the apparatus.

The faucet coupling assembly 14 includes a central elbow member 26 which is formed in a hollow, generally cylindrical configuration and is contoured in an L-shaped orientation. The faucet coupling assembly 14 has an upper section 28 which includes faucet coupling means and a lower section which includes a first compression unit 32. The upper and lower sections each are threadedly coupled to the central elbow member 26. In the preferred embodiment of the apparatus the faucet coupling assembly is fabricated of plastic. Note FIGS. 1 and 4.

The faucet coupling means comprises an inner section 34 which includes male screw threads 35 and an outer section 36 which includes a snap-on coupling. In the preferred embodiment of the apparatus the faucet coupling means is fabricated of elastomeric materials. The male screw threads 35 are coupled within a faucet head. The outer section 36 is securely fastened around a faucet head. The outer section includes cross-hatching 38 to frictionally engage the upper section. This enables a user to tightly couple the coupling means to a faucet. The first compression unit 32 regulates the flow of water through the apparatus. The upper and lower sections have smaller diameter than the central elbow member. This configuration allows a user to, if desired, permanently attach the faucet coupling means to a household faucet. Note FIGS. 1 and 4.

Figure 2:
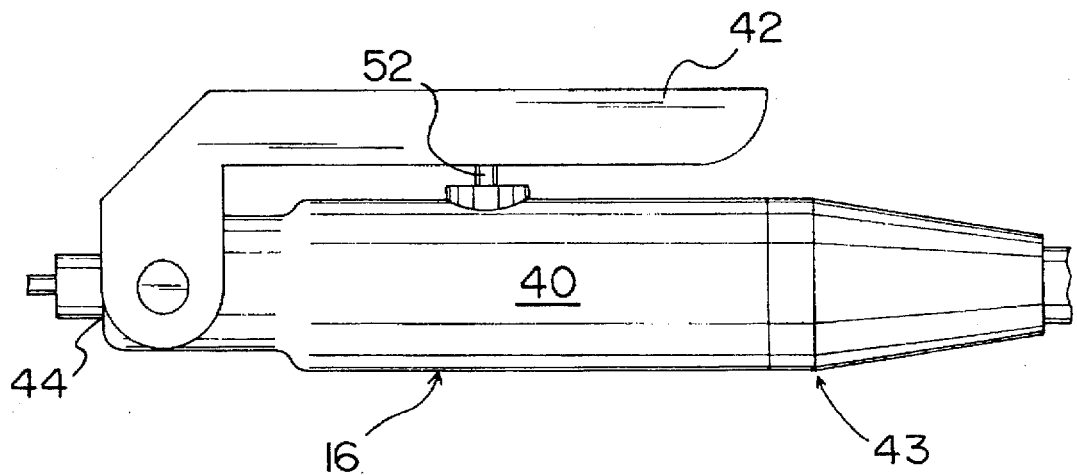
FIG. 2 is a side perspective view of the water control assembly.
Figure 5:
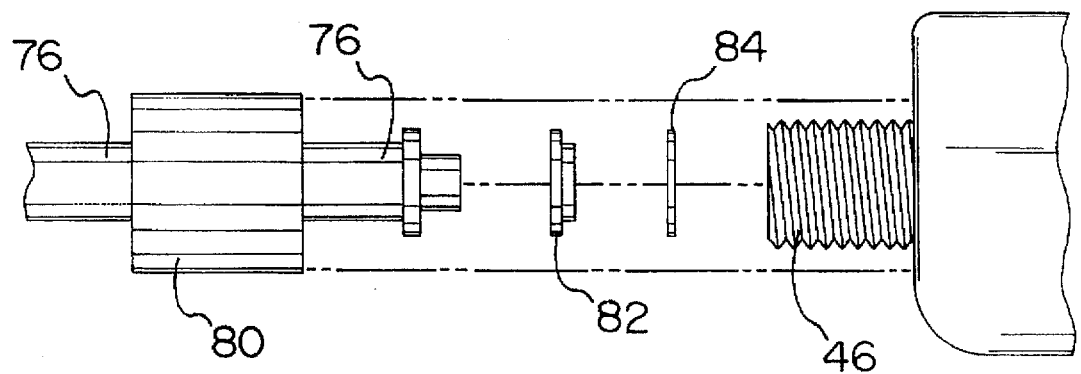
FIG. 5 is a separated perspective view illustrating the positioning of the various components of the copper tubing with respect to the water control device.

The water control handle 16 includes a main body 40 and a L-shaped control lever 42 which is hingedly coupled to the main body. In the preferred embodiment of the apparatus the water control handle is fabricated of plastic. The main body 40 is formed in a generally cylindrical configuration and has a central region, an inboard end 43, an outboard end 44 and a hollow interior. The outboard end includes a projection member 46 extending from it. The projection member has a hollow interior and includes male screw threads. The central region includes a pin 52 projecting from it. In an operative orientation, a user grasps the control lever thereby depressing the pin and actuating the flow of water. Note FIGS. 1, 2 and 5.

Figure 3:
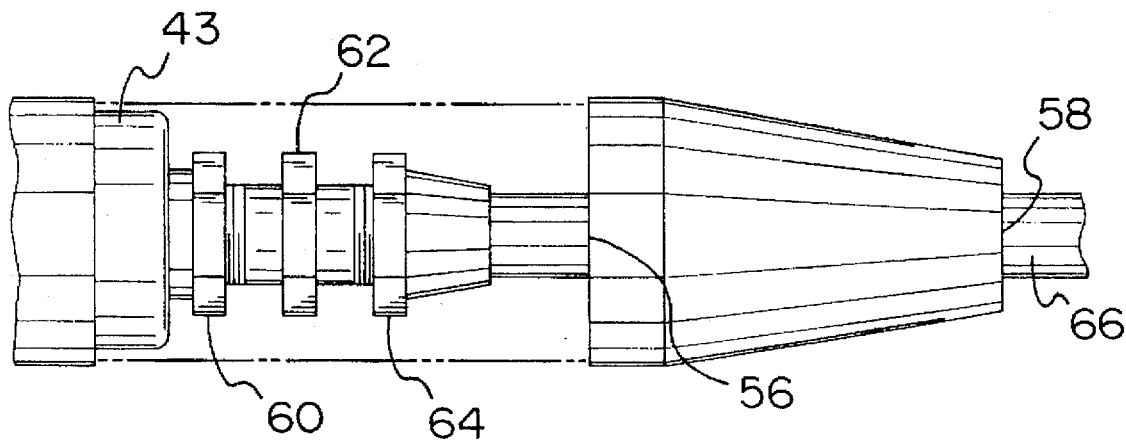
FIG. 3 is a separated perspective view illustrating the internal components of the water control devices.

The inboard end includes a handle sleeve 54 which is formed in a hollow, generally conical configuration with first 56 and second 58 open free ends. The first free end 56 is coupled to the water control handle 16. A reducer 60, PVC tubing 62 and a second compression unit 64 are positioned within the handle sleeve. These act to regulate the flow of water through the apparatus. The compression unit 64 and reducer 60 each are threadedly coupled to the PVC tubing 62. Note FIG. 3.

A flexible rubber hose 19 has an inboard end 65, an outboard end 66 and a length of six feet. The length of the hose allows the apparatus to be used in a variety of locations. The inboard end 64 of the hose is coupled to the first compression unit 32 of the faucet coupling assembly. The outboard end 66 of the hose is positioned through the second free end 58 of the handle sleeve 54 and is coupled to the second compression unit 64. Note FIGS. 1 and 3.

Figure 6:
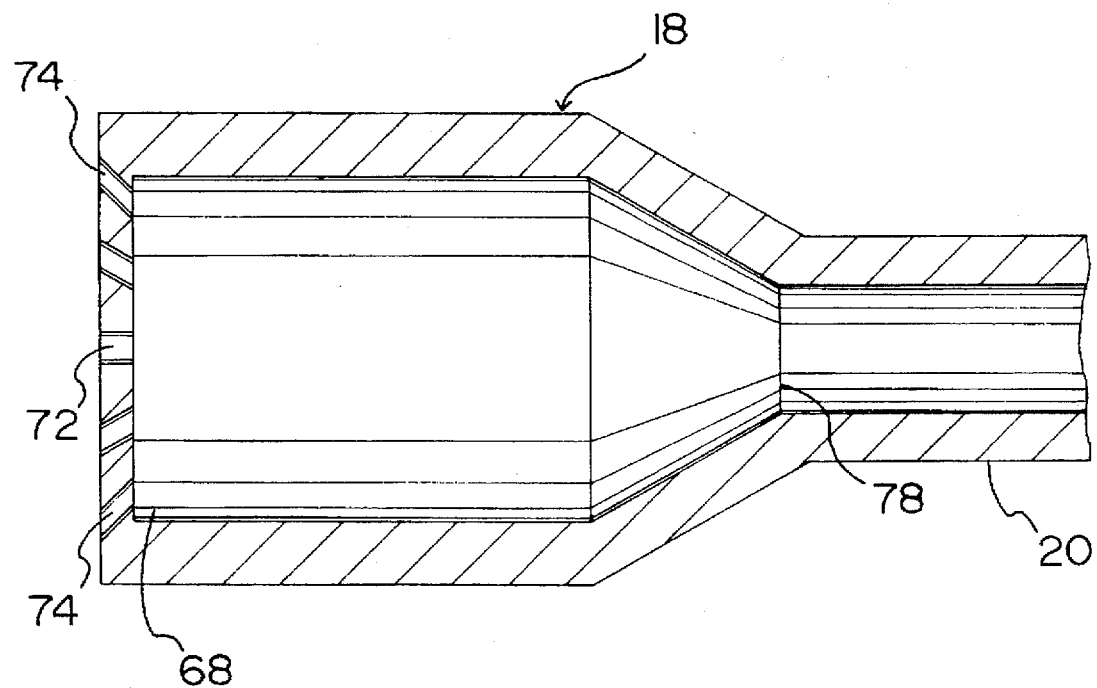
FIG. 6 is a cross sectional view of the spray head of the apparatus.

The spray head 18 is formed in a hollow, generally cylindrical configuration with a upper end 68 and a lower end 70. The upper end 68 has a greater diameter than the lower end. The upper end includes a plurality of water apertures. A central aperture 72 projects vertically. The peripheral apertures 74 project angularly. Note FIG. 6.

Copper tubing 20 is formed in a elongated generally cylindrical configuration and contoured as a loop with an inboard end 76 and outboard end 78. The inboard end 76 is positioned horizontally and includes a nut 80, a rubber seal 82 and a PVC washer 84. The inboard end 76 of the copper tubing is threadedly coupled to the projection member of the handle and secured by the nut. The outboard end 78 of the copper tubing is positioned vertically and is formed contiguously with the lower end of the spray head. Note FIGS. 1 and 5.

In an operative orientation, a user places the spray head 18 within the cylindrical aperture 24 in the colostomy pouch. The user then connects the faucet coupling assembly 14 to a faucet and turns on the water. The user regulates the flow of water with the water control handle 16 and washes the colostomy pouch 12. Note FIGS. 1–6.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A new and improved colostomy pouch rinsing device for use in association with a faucet including a head and water, the apparatus comprising, in combination:

a colostomy pouch formed in a generally rectangular configuration with a front, a top and a bottom, the front including attachment means to couple the pouch to a patient's abdomen, the bottom including a generally cylindrical aperture therein;

a faucet coupling assembly including a central elbow member formed in a hollow generally cylindrical configuration and contoured in an L-shaped orientation, the faucet coupling assembly having an upper section including faucet coupling means and a lower section including a first compression unit, the upper and lower sections each being threadedly coupled to the central elbow member, the faucet coupling means comprising an inner section including male screw threads and an outer section including a snap-on coupling, the male screw threads being coupled within a faucet head, the outer section being securely fastened around a faucet head, the outer section including cross-hatching to frictionally engage the upper section, the first compression unit regulating the flow of water therethrough, the upper and lower sections having a smaller diameter than the central elbow member;

a water control handle including a main body and an L-shaped control lever hingedly coupled thereto, the main body being formed in a generally cylindrical configuration and having a central region, an inboard end, an outboard end and a hollow interior, the outboard end including a projection member extending therefrom, the projection member having a hollow interior and including male screw threads therearound, the central region including a pin projecting therefrom, in an operative orientation a user grasping the control lever thereby depressing the pin and actuating the flow of water;

the inboard end including a handle sleeve being formed in a hollow, generally conical configuration with first and second open free ends, the first free end being coupled to the handle, a reducer, PVC tubing and a second compression unit being positioned within the handle sleeve and regulating the flow of water therethrough, the compression unit and reducer each being threadedly coupled to the PVC tubing;

a flexible rubber hose having an inboard end, an outboard end and a length of six feet, the inboard end of the hose being coupled to the first compression unit of the faucet coupling assembly, the outboard end of the hose being positioned through the second free end of the handle sleeve and coupled to the second compression unit;

a spray head formed in a hollow, generally cylindrical configuration with a upper end and a lower end, the upper end having a greater diameter than the lower end, the upper end including a plurality of water apertures projecting therethrough; and copper tubing formed in a elongated generally cylindrical configuration and contoured as a loop with an inboard end and an outboard end, the inboard end being positioned horizontally and including a nut, a rubber seal and a PVC washer, the inboard end of the copper tubing being threadedly coupled to the projection member of the handle and secured by the nut, the outboard end of the copper tubing being positioned vertically and being formed contiguously with the lower end of the spray head, in an operative orientation a user placing the spray head within the cylindrical aperture in the colostomy pouch, the user then connecting the faucet coupling assembly to a faucet and turning on the water, the user regulating the flow of water with the water control handle and washing the colostomy pouch.

2. A colostomy pouch rinsing device comprising:

a faucet coupling assembly including a central elbow member formed in a hollow generally cylindrical configuration, an upper section and a lower section, the upper section including faucet coupling means and a lower section including a first compression unit, the upper and lower sections each being coupled to the central elbow member;

a water control handle including a main body and a control lever coupled thereto, the main body having a central region, an inboard end including a handle sleeve, an outboard end and a hollow interior, the outboard end including a projection member extending therefrom, the central region including a pin projecting therefrom;

a rubber hose having an inboard end being coupled to the faucet coupling assembly, the outboard end of the hose being coupled to handle sleeve;

a spray head formed in a hollow, generally cylindrical configuration with an upper end including a plurality of water apertures projecting therethrough; and copper tubing with an inboard end being threadedly coupled to the projection member of the handle and an outboard end formed contiguously with the spray head, in an operative orientation a user placing the spray head within a colostomy pouch and connecting the faucet coupling assembly to a faucet, the user regulating the flow of water with the water control handle and washing the colostomy pouch.

3. The colostomy pouch rinsing device as set forth in claim 2 and further comprising:

a colostomy pouch formed in a generally rectangular configuration with a front, a top and a bottom including an aperture, the front including attachment means to couple the pouch to a patient's abdomen, a user placing the spray head into the aperture to effect cleaning of the pouch.

4. The colostomy pouch rinsing device as set forth in claim 2 wherein the faucet coupling means comprises an inner section including male screw threads and an outer section including a snap-on coupling, the male screw threads being coupled within a faucet head, the outer section being securely fastened around a faucet head.

5. The colostomy pouch rinsing device as set forth in claim 4 and further including:

a reducer, PVC tubing and a second compression unit being positioned within the handle sleeve and regulating the flow of water therethrough, the compression unit and reducer each being threadedly coupled to the PVC tubing.

6. The colostomy pouch rinsing device as set forth in claim 4 wherein the rubber tubing has a length of six feet.

7. The colostomy pouch rinsing device as set forth in claim 4 wherein the copper tubing is formed in a elongated configuration and contoured as a loop with an inboard end and outboard end, the inboard end being positioned horizontally and including a nut, a rubber seal and a PVC washer, the outboard end of the copper tubing being positioned vertically.

* * * * *